US008286517B2

(12) United States Patent
Lee et al.

(10) Patent No.: US 8,286,517 B2
(45) Date of Patent: Oct. 16, 2012

(54) AEROSOL PARTICLE DEPOSITION ON SURFACES

(75) Inventors: Sang Don Lee, Chapel Hill, NC (US); Shawn P. Ryan, Durham, NC (US); Emily G. Snyder, Raleigh, NC (US)

(73) Assignee: The United States of America as represented by the Administrator of the U.S. Environments Protection Agency, Washington, DC (US)

( * ) Notice: Subject to any disclaimer, the term of this patent is extended or adjusted under 35 U.S.C. 154(b) by 484 days.

(21) Appl. No.: 12/457,164

(22) Filed: Jun. 2, 2009

(65) Prior Publication Data

US 2010/0300221 A1 Dec. 2, 2010

(51) Int. Cl.
*G01N 33/00* (2006.01)

(52) U.S. Cl. .......... 73/866

(58) Field of Classification Search .......... 73/866; 118/300; 427/421.1
See application file for complete search history.

(56) References Cited

U.S. PATENT DOCUMENTS

| | | | | |
|---|---|---|---|---|
| 4,920,996 | A * | 5/1990 | Flanner | 134/22.11 |
| 5,091,017 | A * | 2/1992 | Flanner | 510/185 |
| 7,363,828 | B2 * | 4/2008 | Liu | 73/863.03 |
| 2005/0028577 | A1 * | 2/2005 | Chang et al. | 73/23.2 |
| 2005/0035221 | A1 * | 2/2005 | Gathright | 239/461 |
| 2007/0166463 | A1 * | 7/2007 | Kelly | 427/345 |

* cited by examiner

*Primary Examiner* — Eric S McCall
(74) *Attorney, Agent, or Firm* — Hendricks & Associates

(57) ABSTRACT

A method and apparatus for generating a standardized surface contaminated by an aerosol deposited on its surface is described. Aerosols are propelled horizontally onto a vertical surface. The standardized contaminated surface is used to evaluate the effectiveness of cleaning and removing techniques.

11 Claims, 6 Drawing Sheets

AEROSOL PARTICLE DEPOSITION ON SURFACES

GOVERNMENT SUPPORT

The work resulting in this invention was supported in part by the Environmental Protection Agency. The Government of the United States may therefore be entitled to certain rights in the invention.

FIELD OF THE INVENTION

The present invention relates to methods and apparatus for simulating natural deposition of aerosols onto target surfaces. Resulting materials provide standards for cleaning, decontamination and/or disinfection.

BACKGROUND OF INVENTION

When determining the effectiveness of the removal of a composition from a solid surface, typically a standardize amount of composition on a standardized solid surface is used in order to compare the effectiveness between two or more removal techniques. A variety of different contaminants contacting a variety of different surface materials have been used as standards for cleaning. Of particular past interest has been in the field of containment and decontamination strategies for the recovery process following an aerosol distribution of hazardous substances, particularly an urban radiological dispersion device (RDD) or a so-called "dirty bomb". The physical impact of an RDD in a given area is a function of the explosive design, the radioactive material type, and weather (e.g. rain and wind). The size and shape of the contaminated area is dependent upon the geometry of the area, the device geometry, the size distribution of the RDD particles and the wind conditions after the explosion. Cleanup after an RDD will likely occur for weeks to months after the event; therefore the contaminated area will be exposed to a variety of weather conditions (rain, snow, relative humidity (RH) variation, etc). This may allow penetration of the water-soluble radioactive material into permeable surfaces increasing the difficulty of removing the contaminant.

Previously, a contaminant was placed in liquid form on the surface, allowed to dry and then used as a standard for measuring the effectiveness of a specific cleaning or removal technique. However, such deposition of contaminant onto a surface is itself not standardized and suffers from uneven adsorption of liquid into the surface, uneven drying, liquid spreading on the surface and uneven surface penetration (particularly for porous surfaces). Also, liquid deposition is not ideal for a standardized representation of aerosol deposition of contaminants onto surfaces. Furthermore the surface will need to be horizontal when adding the liquid, which does not reflect many normally occurring aerosol contamination events.

Aerosols have been used to coat various surfaces to prepare a standardized surface. This has been done using a particle-settling chamber. This chamber contains the target surface(s) at the bottom and particles are introduced into the chamber top. Particles are continuously mixed with air to generate a homogenous mixture for deposition. Deposition occurs by settlement of larger particles onto the target surface(s). This arrangement suffers from lack of standardization because different sized particles or droplets settle at different rates and aerosol diffusion can generate uneven deposition. The method is also time consuming when high surface concentrations are required.

The method is also dependant on the initial particle concentration and the rate of later, additions, air dilution or the mixing method and rate. Differing mixing, diffusion and dilution methods will also cause differing amounts of particle deposition on the sides of the particle settling chamber, thereby preventing that subset of particles from depositing on the target surface(s). Still further, if the particles do not deposit onto the sides of the particle-settling chamber, a greater concentration of certain sized particles that have inelastic collisions with the side walls may be deposited on bottom surfaces adjacent to the side walls and not uniformly over the target surface(s).

Small particles (e.g. less than one micron in diameter) may remain suspended for a very long time (particularly when agitated) and are deposited based on diffusion whereas larger particles are deposited based on gravity caused settling. Very light (low density) particles and charged particles have a similar problem with remaining in suspension for a very long time. Such deposition is hard to control, being based on different properties for different sized or types of particles. Furthermore, the use of a settling chamber does not reflect many real-life aerosol contamination situations.

To overcome these problems, the following invention deposits aerosols onto target surfaces in an easy and controlled manner, which yields a more uniform and standardized test surface sample. Such surfaces provide a better standard control for decontamination of and evaluation of coated surfaces.

SUMMARY OF THE INVENTION

The present invention standardizes the deposition of a contaminant on a surface by forcibly propelling an aerosol at a target so that aerosol deposition is essentially independent of gravity, diffusion and other effects.

The present invention also seeks to mimic the type of aerosol deposition that occurs naturally as the result of accidental or intentional formation of an aerosol, particularly those where the aerosol is propelled laterally against a surface.

The present invention also provides for methods for making an aerosol deposited-standard in a simple, rapid and reproducible manner.

The present invention involves methods and apparatus which may be small in size yet represent events which occur over much longer distances outside by adjusting the amount, distance, pressure used to propel the aerosol processes.

The basic steps in the present invention are generating and propelling an aerosol laterally against a target surface. This is done in a chamber body with contaminant aerosol being propelled from one end to a location adjustable target surface under different amounts, propellant forces and environmental conditions in order to mimic a certain real-life aerosol contamination event.

The present invention is particularly useful for producing standardized surface targets having a standardized contaminant coating, which are useful for testing of different cleaning, decontamination, weathering, disinfecting, wearing, abrading, removal of a thin layer of surface material techniques.

While the present invention is described in terms of a contaminant on a surface, it should be understood that these terms are to be interpreted broadly to include entire classes of materials such as are mentioned below.

DETAILED DESCRIPTION OF THE INVENTION

Figure 1:
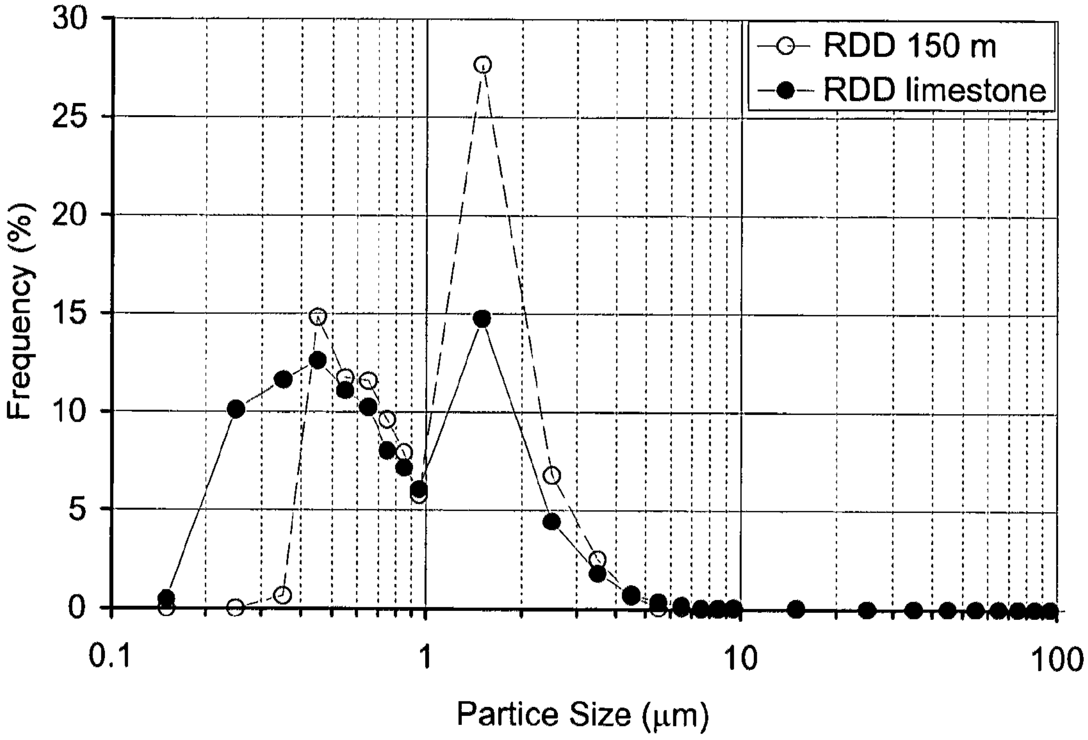
FIG. 1 shows the CsCl particle size distribution from an RDD outdoor simulation test.

A first preferred embodiment of the present invention is the method for preparing the standardized surface having an aerosol deposited thereon. In this method the aerosol is propelled so that it strikes the surface target and is deposited thereon. The purpose of this method is to apply a uniform dispersion of spots on the surface target rather than a complete coating. The pattern formed both mimics the deposition of aerosols in real-life situations as well as forming a uniform pattern of deposited aerosols that can be used as standards. By adjusting the amount of aerosol, the concentration of solid or liquid substances in the aerosol, the distance before the aerosol strikes the target surface and the velocity of the aerosol, one can make a variety of different standards. These standards have many uses, and different standards may mimic different aerosol deposition events occurring in actual events.

The selection of aerosol contaminants, which may be used, is both large and diverse. Viruses, bacteria, fungi, toxins, spores, agricultural chemical sprays such as fertilizers, pesticides, etc. air pollutants (e.g. fly ash, crushed stone (e.g. asbestos), unburned hydrocarbons, etc.), irritating, hazardous and caustic agents, radioactive materials, for example, depleted uranium (from armor piercing weapon), white phosphorous, poisonous liquids (e.g. nerve gas), industrial chemicals, and almost anything which forms an aerosol from a pressurized vessel that has ruptured, leaked or released. Volatile liquids may also be considered aerosols if they remain in liquid form until they are deposited onto the target surface. The same applies for sublimeable solid particles.

Furthermore, substances, including those not normally forming or considered to be an aerosol, are included when they are adhered to or bound to carrier particles, which can form an aerosol and/or carry various chemicals or biologicals in order to deliver them to the target surface.

The surface targeted for aerosol deposition may be almost any solid material and preferably is composed of materials typically subjected to aerosols. Examples include: wood, brick, stone, metal, glass, cloth, vegetation, skin, hair, fur, plastic, paper etc. The target surface may be porous or nonporous. The target surface may be macroporous or microporous to allow movement of gasses but not aerosol particles and thereby act as a filter. A vacuum can suck the gas and thereby propel aerosol particles toward the target surface. This filter deposit of the aerosol is another means for controllably propelling the aerosol particles against the target surface. The resulting product is a standardized contaminated surface, which may be used for a variety of uses including for evaluating protective gear (e.g. lab goggles), pesticidal effectiveness and amount applied vs. coverage and a removal of the contaminant by physical removal techniques. Also, the effectiveness of various inactivation techniques, for example, heat, chemical, biological, radiation inactivation treatments may be evaluated.

Since the contaminant removal methodology is dependant on the type of contaminant and the type of surface upon which it is deposited upon, a wide variety of different combinations of contaminants and surfaces may be used for generating a number of different standards.

Furthermore, the aerosol deposition conditions may be changed to reflect natural differences in the air and to mimic different aerosol deposition situations. Representative differing conditions and methods include: different compositions of the aerosols, different pressures of the aerosol, different size of aerosol particles, different amounts or concentrations of substance in the aerosol particles, different velocities of the aerosol particles striking the surface target, different dispersion pattern of aerosol on the surface target, and different atmospheric conditions of temperature, humidity, barometric pressure, wind, etc.

In any given decontamination protocol, it is expected that more than one combination of standardized contaminated surface will be used for comparison. Each standardized contaminated surface may be the same or vary in surface type and composition as well as amount, concentration and type of contaminant and aerosol deposition conditions. Pluralities of these standardized surface targets may be included in a set and optionally packaged together into a kit along with appropriate labels or markings and optionally with instruction and explanations of the surface targets.

The standard contaminated surfaces of the present invention are designed to mimic real-life situations resulting from biological, mechanical or fluid propelling, explosions, splattering, etc. from accidental, intentional or natural aerosol generation. For example, a person infected with influenza who sneezes generates an aerosol, which is propelled into the surroundings and may be deposited onto body parts of the person or others nearby. The aerosol may also be deposited on inanimate objects such as door knobs, furniture, keyboards etc. When such an aerosol is deposited onto dust and other small particles, it may be suspended in air or, if settled, resuspended to form an aerosol if agitated mechanically or by air movement.

While the present specification uses the term "contaminant", its common definition is too narrow for the purposes of the present invention. A "contaminant" in intended to encompass any unwanted solid or liquid material that is or can be adhered to a solid surface.

In the specification the term "removal" is intended to encompass physical removal or alteration so that the contaminant is no longer in the same form as it was when deposited. For example biological contaminants may be killed or chemically altered to become inert. Chemical contaminants may be neutralized, degraded, chemically altered or bound so that they display different chemical or bio-affecting properties. A variety of physical removal techniques may be used such as cleaning, abrading, scraping, physical removal of a thin layer of the target surface material, burning off by heat, adding reactive chemicals to remove a thin layer of the target surface material (e.g. acid wash). Some techniques may involve more than one "removal" method such as normal weathering of outdoor surfaces where rainwater may dissolve, wind and particles in it may wear, air pollutants may coat or react with and sunlight (both heat and ultraviolet light effects) may chemically degrade the contaminant.

While not normally considered a removal technique the present invention includes techniques to encapsulate or otherwise seal the contaminant to prevent it from interacting with the surrounding environment. For example, the standardized contaminated surfaces may be painted or otherwise covered with an adhering material to prevent contact with the contaminant. It is preferred that the covering adhere permanently to the surface and/or contaminant. The standardized contaminated surfaces may also be used to evaluate the effectiveness of such encapsulating techniques. The effectiveness of these techniques and the removal techniques mentioned above may be best determined using one or more or an entire set of the standardized contaminated surfaces as both a test sample and a control.

When the target surface is porous, the velocity of the aerosol may affect penetration of the surface. This parameter may be controlled by a variety of different velocities and particle sizes used to generate standards having different degrees of penetration. Aerosol may be propelled such that it is deposited into fine indentations or imperfections on the surface. These may be treated in the same manner as depositing onto a porous surface. Also, depending on the chemistries of the target surface and aerosol material, diffusion into the target may also occur and this would be variable on a number of local environmental factors as well as all of the previously mentioned determinants of deposition onto non-porous solid surfaces.

Aerosols in the present invention may be made of solid particles or liquid droplets. Both charged and uncharged aerosols may be used.

For charged aerosols, the target may be neutral or have an opposite or same charge applied to it in varying amounts to standardize deposition or to simulate an actual situation. Also, the insides of an aerosol deposition chamber may also be charged to discourage deposition on the sides. The chamber walls beyond the target or behind the nozzle discharging the aerosol may also be charged to enhance or retard aerosols from being deposited onto the target. The charge effects may also be used to propel or assist in propelling the aerosol onto the target's surface.

A number of different means may be used to generate aerosols for used in the present invention. These may be used individually or in combination. While a metered dose inhaler type is exemplified, one may also use atomizers, nebulizers, corona discharge, compressed air, etc. A nozzle is used to direct the propelled aerosol toward the target surface. The nozzle may be inert to the aerosol or it may generate or modify the spread or other properties of a cloud of propelled aerosol.

Standardized aerosol contaminated surfaces generally have much less than complete coverage of the surface by the contaminant. An aerosol by its very nature has gas between individual particles and the gas is generally not deposited onto the target surface.

The aerosol may be propelled by pressurized gas, chemical reaction, heat/boil, physical movement (e.g. fan, pressurized movement through a small nozzle, movement of the target into a cloud of aerosol), electric field if the aerosol particles are charged, magnetic field if appropriate particles are used and vacuum evacuation of the aerosol deposition chamber.

The aerosol may be formed from a solution or suspension of solids or immiscible liquids in a carrier liquid. The aerosol may also be formed by solid particles or liquid droplets suspendable in the gas. Further, liquids may be volatile so that as the aerosol is being formed, the liquid component is removed.

Figure 2:
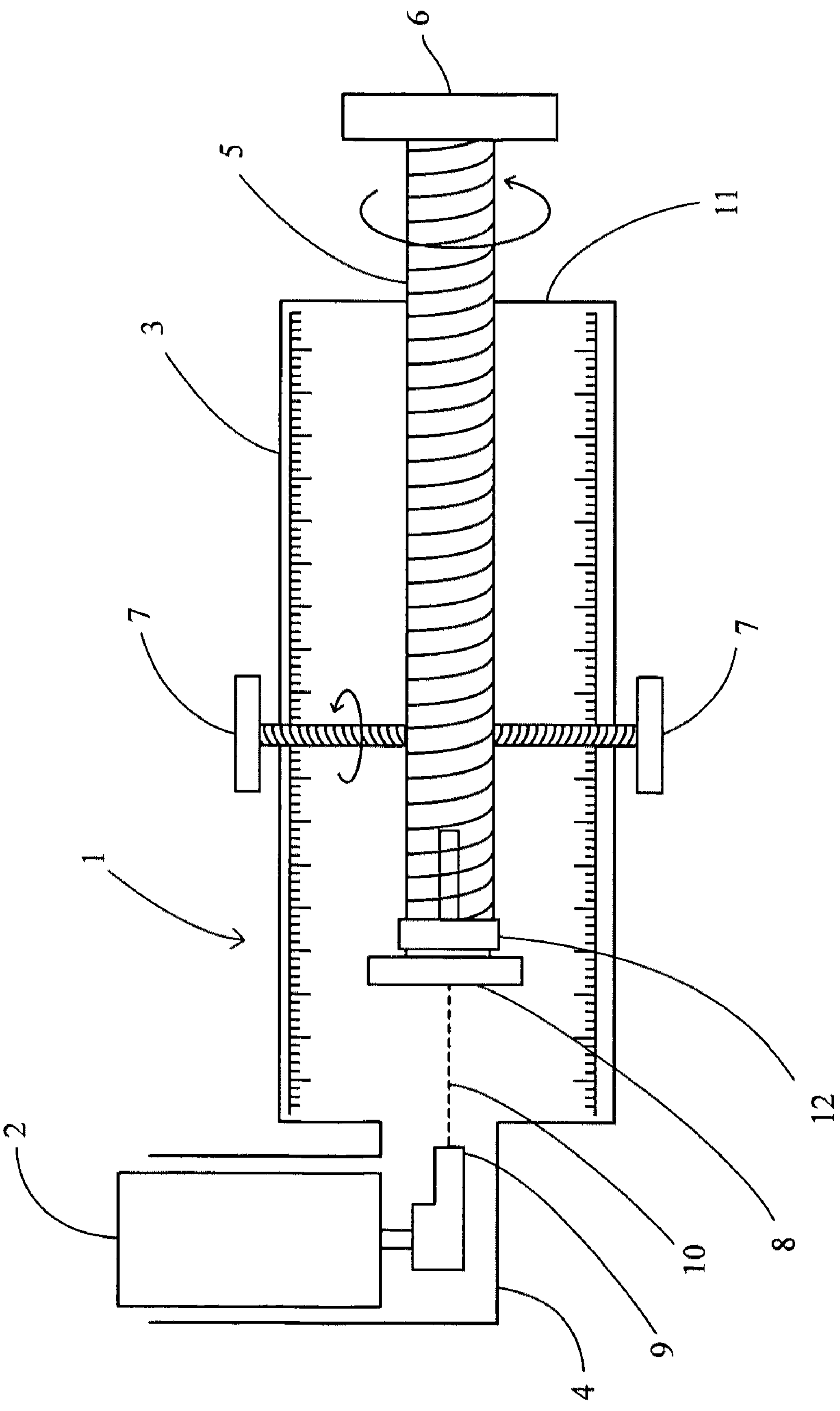
FIG. 2 is a schematic diagram of a particle deposition chamber using MDL.
Figure 6:
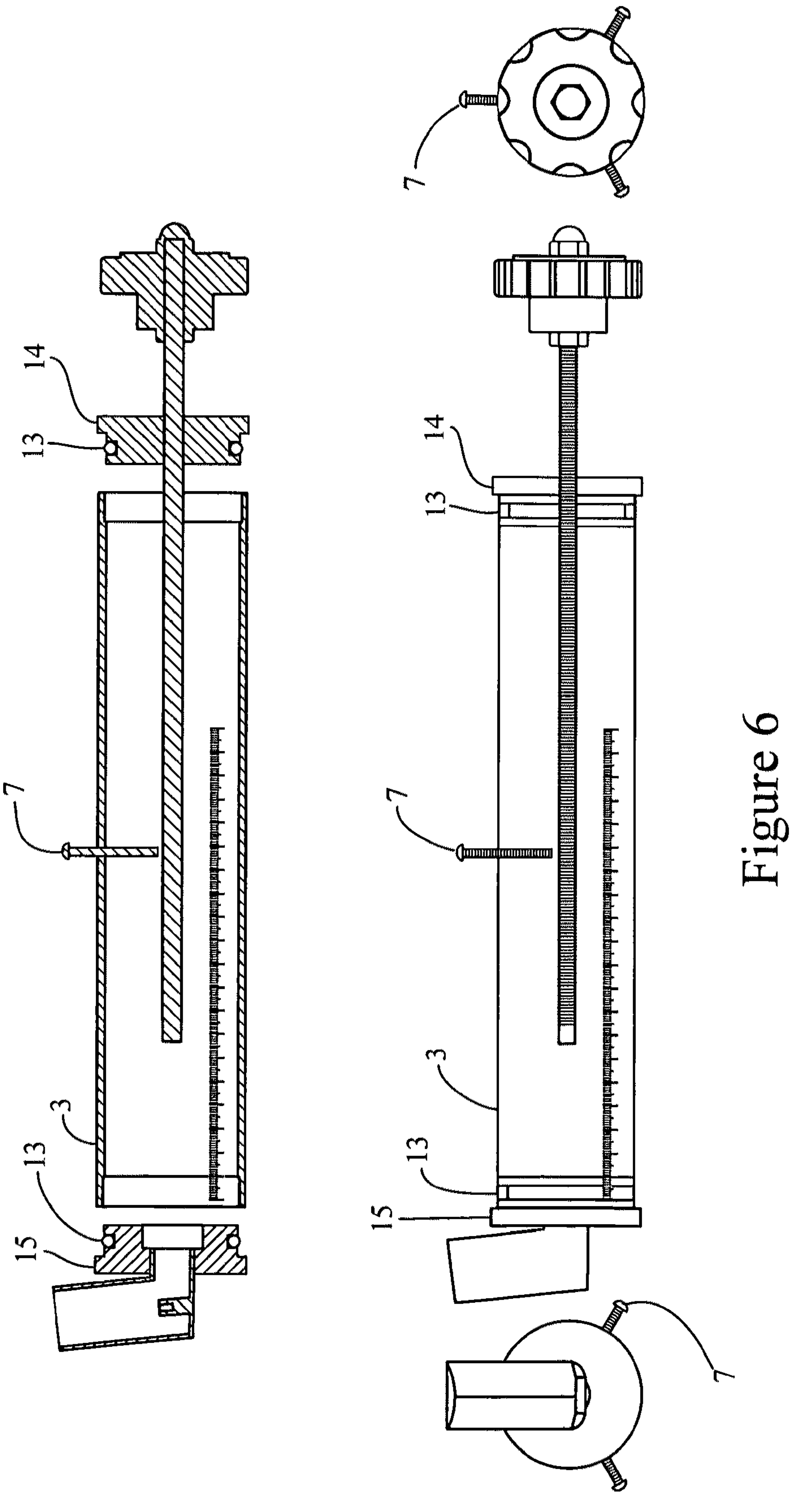
FIG. 6 is a schematic diagram of a particle deposition chamber.

A second preferred embodiment of the present invention is an apparatus for aerosol deposition by propelling the aerosol against the surface of the solid target. The apparatus may be in the form of anything that can perform the methods described above. An example is depicted in FIGS. 2 and 6.

In this embodiment, a bench-top particle deposition system (1) has an aerosol generating means (2) to propel an aerosol laterally (roughly horizontally) along a path (10) into a plastic chamber body (3) towards a target substrate (8). The aerosol generating means (2) is held in a fixed position by an adapter or actuator (4). The target substrate (8) is held at a fixed distance from a nozzle (9) of the aerosol generating means. The substrate is held attached to a stub (12) located at the end of an adjustable substrate holder (5). The length of the path (10) is adjustable by adjusting the substrate holder (5) using a distance-adjusting knob (6). The substrate holder is threaded along its shaft with meshes with female threads in an end (11) of the chamber body (3). A plurality of center aligning screws and knobs (7), for aligning the substrate holder (5) so that the target substrate is placed into the path (10) of aerosol dispensed from the aerosol generating means (2). The adapter or actuator (4) may be connected to the chamber body (3) by an adapter end cap (15), which may have an O-ring (13) for maintaining a gas-tight seal. The end (11) of the chamber may optionally be an end cap (14), which also may have an O-ring (13) for maintaining a gas-tight seal.

Representative sizes for the system would be a 5 cm diameter chamber body (3), which is 12 cm long. The substrate holder (5) may be a ⅜-16 threaded rod and the aligning screws and knobs (7) may be 6-32 locating screws. Preferably at least three aligning screws and knobs (7) are present to align the target substrate (8) in both X and Y directions perpendicular to the path (10).

A third preferred embodiment of the present invention is an alternative use for the methods and apparatus described above. While the path of propelled aerosol is depicted as moving laterally in a roughly horizontally direction, this need not be so. In real-world deposition of aerosols, the aerosol may be propelled in any (or every) direction. The present invention may be tilted or even propelled vertically (up or down) in order to mimic actual aerosol deposition events. The effects of gravity may be insignificant over the short distances and time periods involved or conditions may be adjusted to allow for the effects of gravity or settling. For simplicity sake, the drawings depict a horizontal propelling of contaminant onto a vertical surface but alternative positions are useful.

The nozzle may allow an even spread of the aerosol to completely cover the target surface. Alternatively, the nozzle and other conditions may be varied to provide an intentionally uneven distribution over the surface. An example is to provide for gas flow in the aerosol depositing chamber independent of the aerosol flow. Including cross-flow of air may simulate wind. Also, the airflow may be counter-flow or co-flow. Such actions may even be a part of the propelling of the aerosol. Movement of either surface or aerosol generator/nozzle may simulate the effects of aerosol deposition on a moving object. Note that patients with influenza will not only propel an aerosol of virus but a co-flow of air movement and perhaps a movement of the patient's head may occur simultaneously. Likewise for inhaling of any aerosol and its deposition on the inside surfaces of the upper or lower respiratory track. As a purpose for the standardized contaminated surfaces is to mimic actual events outside a lab setting, many variations may be used alone or in combination.

It is another embodiment of the present invention to mount the surface target at a slanted angle with respect to the aerosol flow path inside the aerosol deposition chamber. Instead of a uniform coating, a gradient of contaminant may be deposited on the surface. Such a target may be used in lieu of a plurality of targets where each surface has a different amount of contaminant deposited on it.

A fourth preferred embodiment of the present invention is the mimicking of the result from an explosion or a weapon.

Because of the many factors involved, it is important to have various standards mimicking aerosol dispersion in order to properly evaluate various decontamination methods. Particularly with the use of a RDD in an outdoor environment, it is necessary to understand the interactions between these surfaces and the contaminant to develop optimized strategies to prevent the spread of radionuclide contamination and its penetration into, as well as its binding to, urban surface materials. This need led to the present invention.

For the aerosols used in the present invention, a radionuclide of particular interest was cesium, in the form of CsCl, and its interactions with urban materials (such as concrete, limestone, brick, granite and marble) due to its availability and interaction with concrete and limestone. Other heavy metals in soluble or particulate form may also be used. Also, other salts of the metals (e.g. nitrates) may also be used depending on the solubility of the liquid. For aerosol solutions, suitable metals and their salts may be chosen based of their stability and ease of forming small particles suitable for forming an aerosol.

The penetration of Cs into building materials is a function of both the ion diffusivity through pores and the ion surface interactions (Q. H. Hu and J. S. Y. Wang, Critical Reviews in Environmental Science and Technology 33, 275-297 (2003) and A. Atkinson and A. K. Nickerson, Radioactive Waste Management 81, 100-113 (1987).). The characteristics of RDD particles (e.g. size and shape) may influence the radionuclide ion penetration through porous building surfaces. Therefore, the present invention mimics the most probable RDD explosion Cs particle deposition process. In the following examples, the size of the particles resulting from the simulated RDD outdoor release were measured and a laboratory method to reproducibly deposit similarly sized Cs particles onto building material coupons was developed.

Identifying the mechanisms of penetration is desirable for predicting the fate of Cs in the urban environment. Due to the heterogeneity of the micro-pore channels, cracks, and varied adsorption sites within the coupons, one-dimensional (line scanning) transect measurements through the coupon may not yield a complete picture of Cs migration. A 2-D mapping (areal scanning) technique for common urban building materials using laser ablation inductively coupled plasma mass spectrometry (LA-ICP-MS) was developed at the United States Geological Survey and can be used to map Cs concentration in building material coupons. Early Cs-contaminated limestone coupon mapping efforts showed that Cs bonded to clay mineral inclusions within the limestone. This is probably due to preferential sorption of the Cs to the clay inclusions over other components of limestone (EPA, "Understanding Variation in Partition Coefficient, Kd, Values, Volume II: Review of Geochemistry and Available Kd Values for Cadmium, Cesium, Chromium, Lead, Plutonium, Radon, Strontium, Thorium, Tritium (3H), and Uranium" (1999)). To explore the penetration process in other building materials, preferential binding of Cs in building materials was studied by estimating the distribution of Cs concentration between water and powdered building materials such as concrete, brick, limestone, granite and marble.

The same type of analysis may be applied to aerosol forming chemical or biological weapons and accidental explosions, for example, bacteria, fungi, toxins, viruses, spores, chemical irritants (e.g. tear gas, blister agents) poisonous liquids, caustic liquids and flammable particles and liquids.

EXAMPLE 1

RDD Outdoor Simulation Test Results

Simulated RDD tests were conducted by preparing nonradioactive cesium chloride (CsCl) and explosive materials. A set of 24 limestone coupons oriented vertically was positioned at ground level 10 m away from the explosive device. The particle size distribution resulting from CsCl explosion particles on one of these limestone coupons is shown in FIG. 1. Particles from the explosion were also collected 150 m from the device using 37 mm polycarbonate 0.4 μm pore size filters (SKC Omega Specialty, PA) connected to air sampling pumps (AirChek 2000, SKC Omega Specialty, PA). The particle size distribution for these Cs particles is also shown in FIG. 1. These outdoor RDD simulation test results demonstrated that the diameters of Cs particles deposited on limestone coupons are less than 10 μM (apparent particle size estimated from electron microscopy).

Particle size data were obtained using the computer controlled scanning electron microscopy (SEM, PSEM, Aspex Instruments, Delmont, Pa.) coupled with energy dispersive X-ray spectrometry (EDX, Aspex Instruments, Delmont, Pa.). The automatic analysis included the identification of Cs, particle diameter determinations, shape determinations (roundness), and locations of each Cs particle. The SEM/EDX was operated in the backscattered electron mode with a 0.1 atm chamber pressure and a 16 mm working distance.

The particle diameter was estimated from the average value of 16 diameters through the individual particle's projected area. A particle was designated a Cs particle if 5% of its total X-ray diffraction signal could be attributed to Cs. Approximately sixteen thousand particles were analyzed to identify the Cs particles and their size distribution on the limestone coupons. EDX determined that approximately 12,000 of these particles were classified as Cs particles. The geometric mean diameter of Cs particles was 0.70 □m with a geometric standard deviation of 2.0.

Ten thousand particles were analyzed to identify the Cs particles and their size distribution on the filter. EDX determined that approximately 7,000 of them were classified as Cs particles. The geometric mean size and geometric standard deviation of Cs particles were 0.9 μm and 1.8 respectively.

EXAMPLE 2

Bench Top Scale Cs Particle Deposition System

For bench scale experiments, a method has been developed to deposit Cs particles on targeted urban building surfaces. Metered dose inhalers (MDIs) were prepared by the aerosol science laboratory at Edgewood Chemical and Biological Center (ECBC). Each MDI contains CsCl saturated (at 20° C.) methanol (analytical reagent grade, Mallinckrodt Inc., KY) solution and propellant gas (pentafluoropropane, HFC-245fa). Methanol was used to dissolve CsCl and to allow the Cs particles to dry quickly either before or after deposition on the building material.

A tube-type acrylic plastic chamber was designed to deposit Cs aerosols generated using the MDI on to 40 mm diameter on circular solid substrates. The chamber is composed of three major parts: a 12 cm-long cylindrical body with 5 cm inner diameter, two lids for MDI adapter (or actuator), and a substrate holder with a distance-adjustable bar. The diagram of this chamber is shown in FIG. 2.

A laser pointer is used to align the center of MDI adapter nozzle with the center of the substrate. The center of substrate holder is aligned to the laser pointer using three center aligning knobs as shown in FIG. 2. The general physical configuration and operation of MDIs are described in S. P. Newman, Respiratory Care 50, 1177-1190 (2005).

Figure 3:
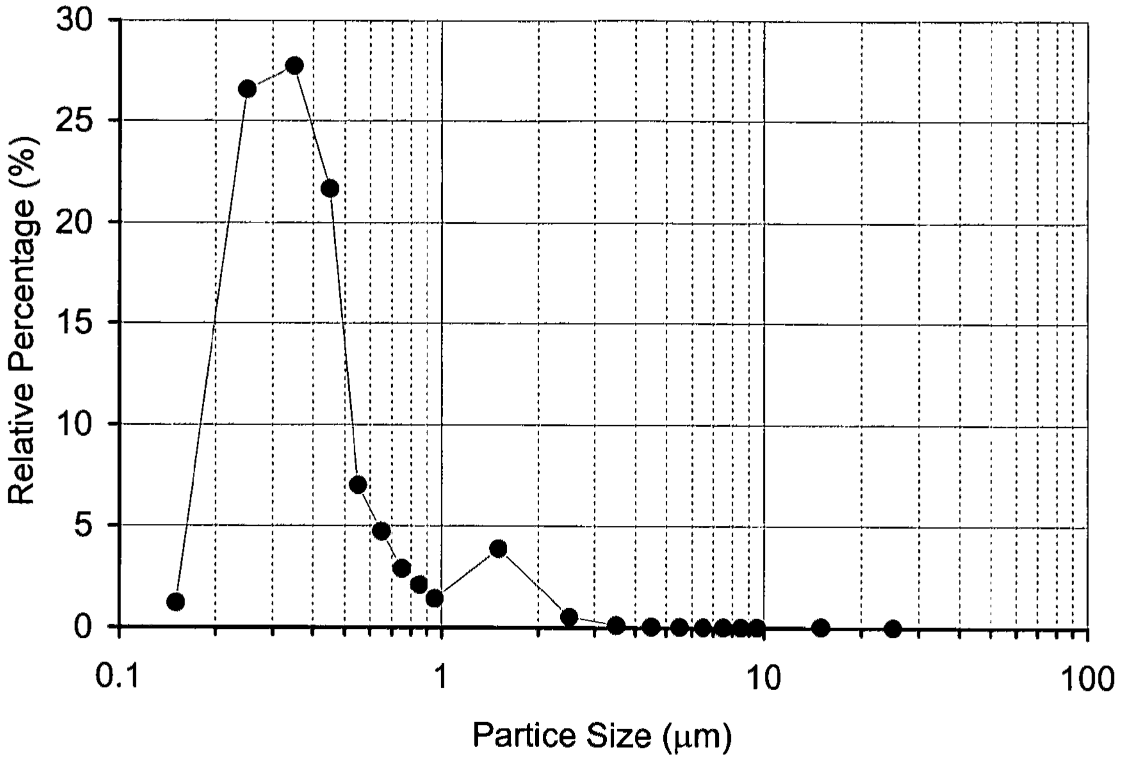
FIG. 3 shows the CsCl particle size distribution from a MDI.

To confirm the composition, shape, and size of the MDI generated Cs particles the MDI was directly puffed onto a 25 mm-diameter aluminum stub. This stub was then analyzed using the same method outlined for analysis of the Cs particles resulting from the RDD simulation test (computer controlled SEM/EDX). A total of 20,000 particles were analyzed on the substrate and 16,000 of them were classified as Cs particles. The size distribution of Cs particles from an MDI actuation is shown in FIG. 3. The geometric mean diameter of this distribution is 0.4 μm, with a geometric standard deviation of 1.6. The RDD simulation test particle size distribution was not perfectly simulated due to the large number of smaller particles produced by the MDI inhaler. The present invention, however, yields the closest particle size distribution on a surface without using water as the solvent for the CsCl. The use of water as a solvent would introduce the possibility of deposition of aqueous particles on the surface, which would not accurately simulate dry deposition.

EXAMPLE 3

Comparison of Different Tests

Figure 4:
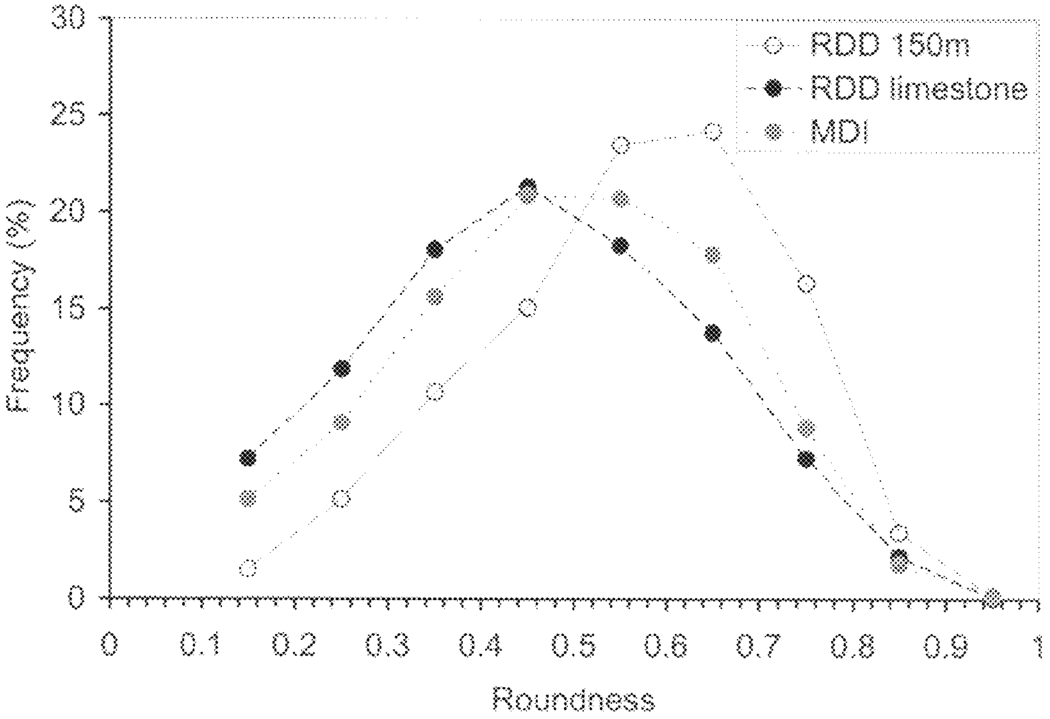
FIG. 4 shows a roundness comparison of CsCl particles from a RDD and a MDI.

Particle shapes from the RDD simulation test and MDI experiment were compared and are shown in FIG. 4. The roundness (circular particles have the roundness close to 1.) of each Cs particle was estimated by the automated SEM/EDX system using the following equation:

$$\text{Roundness}=(\text{perimeter of a particle}/2\pi/(\text{area of a particle}/\pi)^{1/2}$$

The difference in roundness between the Cs particles deposited onto the limestone coupon and the Cs particles deposited onto the filter was an artifact of the pore size limitation of the filter, which allows the filter to collect particles greater than 0.4 μm in diameter. This means that the perimeters of the particles on the filter will be biased and will appear to increase the overall roundness factor as demonstrated in FIG. 4. This roundness distribution data also confirmed the similarity of Cs particle shapes from two different sources (outdoor explosion test and the MDI). The similarity of the particle morphology (roundness) indicates that the MDI-generated Cs particles serve as a suitable simulant for RDD particles generated from an explosion.

While the present invention has limitations regarding the degree of homogeneous particle deposition over the entire surface area and some uncertainty associated with depositing these particles on rough surfaces. In addition, counting of the particles deposited on rough surfaces via the computer controlled SEM will be inhibited by the inability to focus on particles at a range of distances from the detector. It is preferred to analyze at least 1,000 to 2,000 particles to have confidence that the appropriate particle size distribution is represented. However, on the rough surfaces this will require refocusing of the SEM numerous times; therefore, it is probable that these coupons will be difficult to analyze using the automated SEM and may require manual counting in order to characterize the deposited Cs particles.

EXAMPLE 4

Characterization of Cs Subsurface Penetration Using LA-ICP-MS

This method was developed to map the distribution of trace elements within urban building materials using laser ablation (193 nm, UP193FX, New Wave Research, CA) coupled with ICP-MS (Elan DRC-e, PerkinElmer, Conn.). Two major building materials (concrete, and limestone) were mapped to test the method. The laser ablation parameters for each material are summarized in Table 1.

TABLE 1

Laser ablation system parameters

| Laser System | concrete | red brick | limestone |
|---|---|---|---|
| Spot Size | 100 μm | 100 μm | 150 μm |
| Scan Speed | 30 μm/sec | 30 μm/sec | 50 μm/sec |
| Line Spacing | 120 μm | 120 μm | 200 μm |
| Pulse Frequency | 10 Hz | 10 Hz | 10 Hz |

The ablated materials were carried by helium gas to the ICP-MS at a flow rate of 0.8-0.9 $L\cdot min^{-1}$. The argon auxiliary gas flow rate was 0.8 $L\cdot min^{-1}$ and a total 39 nuclides were analyzed from $Li^7$ to $U^{238}$ by the quadrupole mass spectrometer. The system was calibrated with a NIST610 glass standard and validated with NIST Limestone 1c and a US Geological Survey carbonate prototype reference material, MACS-3.

The sources of the test building materials as well as basic information about the materials are shown in Table 2. A block of each material was further prepared by cutting it to fit in the laser ablation chamber. A diamond saw was used to reduce the size of the same and to cut the coupons in half to obtain cross sectional measurements (which indicate penetration). A diamond saw was chosen over other coupon preparation techniques because it is able to generate the smooth surfaces needed for reproducible laser ablation. The sliced surfaces were thoroughly cleaned with the compressed air before analysis to remove possible residue particles.

TABLE 2

Building material descriptions and sources.

| Material | Name | Locality | Source |
|---|---|---|---|
| concrete | QUIKRETE mix | Not Applicable | Home Depot, Idaho Falls, ID |
| red brick | Paving brick | Made from North Carolina red Triassic clay | Triangle Brick Company, Durham, NC |
| limestone | Indiana | South central Indiana | Cathedral Stone Products, Hanover Park, MD |

Maps of representative elements from each material were made. The final dimensions of coupons the 2.5 mm×20 mm, 2.5 mm×18 mm, and 3 mm×5 mm (W×L) for concrete, red brick and limestone coupons respectively.

Element maps of the concrete coupon clearly demonstrate the location of aggregates and the relative composition of each element in the aggregates.

Representative elements in blank red brick coupon were also measured. Cs map shows more homogeneous distribution than the one in concrete and several spots in the element maps show clear spatial correlation of Cs and Al.

The blank limestone coupon maps are relatively simple compared to the concrete or red brick coupon maps likely because of its dominant constituent with calcium carbonate. It is evident that several elements (Al, K, and Fe) are collocated in the same area within the map. This implies there are mineral inclusions in this limestone coupon.

One limestone coupon from the outdoor Cs RDD simulation test was analyzed using the LA-ICP-MS mapping procedure. This coupon was horizontally positioned on the ground at 10 m away from the explosion. As detailed in R.

Fischer and B. Viani, in *Decontamination of Terrorist-Dispersed Radionuclides from Surfaces in Urban Environments*, Research Triangle Park, N.C., 2007, this limestone coupon was conditioned at 83 RH % for 28 days before the test and for 13 days after. After the RH conditioning was complete, the coupon was dry-sliced with a diamond saw and the cut surfaces were thoroughly cleaned with compressed air before analysis. The elements mapped using the LA-ICP-MS were identical to those mapped for blank limestone coupon analysis. The total analyzed area for the Cs contaminated limestone coupon was 6 mm×12 mm (W×L).

EXAMPLE 5

Cesium Chloride Particle Deposited Limestone Elemental Maps from RDD Simulation Test As mentioned in Example 4, several elements are collocated in specific areas of the analyzed coupon surface. A Cs concentration gradient is also observed from the exposed surface to the inside of the limestone coupon. Regions of concentrated Cs are noticed within 2 mm of the exposed surface and these regions are associated with the regions of elevated Al concentration. The collocation of the Cs with aluminum was not observed in the blank limestone coupon element maps. The association of Cs and aluminum rich areas may be due to Cs adsorption to mineral inclusions in limestone.

Limitations of these analyses are related to quantification and contamination. Availability of reference materials that match the coupon both chemically and physically (grain size, density, etc.) is always a concern with LA-ICP-MS analyses. The use of the 193 nm LA system reduces some of the matrix dependence (see Eggins, 1998, Sinclair et al. 1998, Gunther and Heinrich, 1999 and Koenig, 2008). In the case of limestone building materials where the coupon is predominantly a uniform matrix of calcium carbonate, a number of calibration materials are available. The use of a carbonate reference material such as NIST 1c or 1d is possible. However the levels of concentration of analytes of interest may be too low relative the values in the intended study. For example the Cs content of NIST 1c is around 0.5 ppm. This value is low when considering contaminated values may be up to 2 orders of magnitude higher. The use of NIST610 glasses has been validated for carbonate materials when using 193 nm (Sinclair et al., 1998).

Some additional concerns utilizing this mapping methodology include those of contamination. Smearing of Cs particles during cutting or coupon handling is possible. Preliminary testing of laser pre-cleaning indicates that surface contamination is minimal.

The aggregate nature of the concrete makes this material far more complex than limestone. The blank concrete coupon shows the complexity of the chemical and mineralogical heterogeneity of concrete. Quantification of the different phases of the concrete is more difficult.

Element maps demonstrated the potential correlation of mineral inclusions in limestone with the presence of Cs. X-ray diffraction (XRD) identified this mineral as illite, a clay mineral. Numerous studies have previously demonstrated the high affinity of Cs to clay minerals through estimations of distribution coefficients are for Cs in water (K. Akiba, H. Hashimoto, and T. Kanno, Journal of Nuclear Science and Technology 26, 1130-1135 (1989) and R. M. Cornell, Journal of Radioanalytical and Nuclear Chemistry 171, 483-500 (1993).). However, this information is not fully applicable to the general building materials which are a combination of a variety of minerals (M. Konishi, K. Yamamoto, T. Yanagi, and Y. Okajima, Journal of Nuclear Science and Technology 25, 929-933 (1988). Therefore, it is important to estimate the distribution coefficient for urban building materials to fully understand the fate of Cs after deposition.

EXAMPLE 6

Comparative Results Summary

The Cs particle deposition system of Example 2 and the resulting particle size distribution was evaluated compared to the Cs particle deposition resulting from the outdoor explosion test of Example 1. Particles deposited using the benchtop system of Example 2 showed similar characteristics to the outdoor RDD explosion test Cs particles.

The LA-ICP-MS method was able to generate 2-D maps of the target elements, which comprise the various building materials. These maps are useful for understanding the Cs penetration mechanism through porous building materials. According to the limestone RDD simulation test coupon Cs map, Cs transport through the limestone subsurface is significantly influenced by the existence of mineral inclusions. It is hypothesized that these inclusions provide adsorption sites that delay the penetration time or depth and at the same time provide strong binding sites for the Cs. The existence of strong binding sites may increase the level of difficulty in decontaminating the surfaces using conventional methods. Furthermore, information on Cs and building materials binding properties will helps develop optimal decontamination technologies and strategies.

EXAMPLE 7

Comparison of Different Contamination Methods

Figure 5:
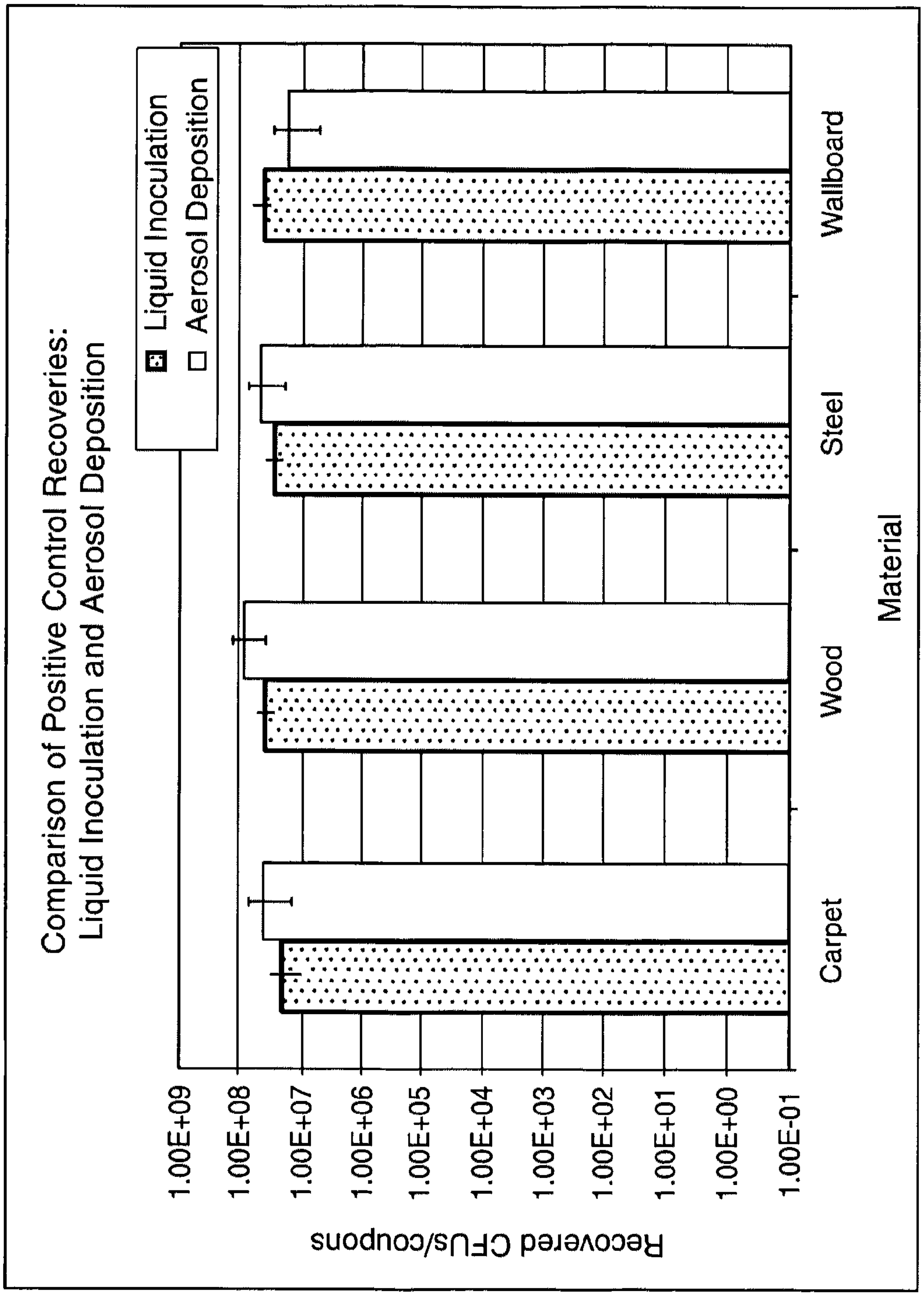
FIG. 5 shows comparative data between the prior art and the present invention contaminated surfaces.

The method of Example 2 was used with *B. subtilis* (ATCC 19659) spores to perform aerosol depositions. The same amount of spores was inoculated by spreading a liquid suspension over identical target surfaces. 18 mm diameter coupons of carpet, wood (pine), galvanized steel (ductwork), and wallboard (latex-painted) were used producing 132 coupons for each test. After deposition or inoculation, recover of the microorganism was attempted and the colony counts for each are shown in FIG. 5.

EXAMPLE 8

Comparison of Different Inactivation Results

The carpet coupons produced by both methods in Example 7 were fumigated with 750 ppmv of $ClO_2$ followed by attempts to recover bacteria from contaminated and fumigated carpet. The bacteria on the aerosol deposited coupons were completely inactivated (no colonies recovered) much sooner than liquid inoculated carpet coupon. In liquid inoculated carpet coupon, about 10,000 colonies were recovered even after fumigating for twice the time needed to completely inactivate all bacteria in the aerosol deposited carpet coupon.

Likewise, the carpet coupons were sprayed with pH-adjusted bleach solution having a pH of 6.8 (+/−0.05) and a final chlorine content of 6000-6700 ppm. Each coupon was wetted by spray of the bleach solution and maintained continuously wet by re-spraying at defined intervals. At designated time periods, the coupon was washed, diluted and bacteria cultured therefrom. After one hour, the bacterial colony count from aerosol deposited carpet coupons had decreased by about two orders of magnitude. By contrast the liquid inoculated carpet coupons had decreased by less than one order of magnitude.

The experiments were repeated by immersion into the pH-adjusted bleach solution. Immersion was consistently better than spraying at inactivating *B. subtilis* for all 8 types of samples after one hour. However, inactivation was consistently higher for aerosol deposited coupons than for liquid inoculated coupons for different types of materials.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

All patents and references cited herein are explicitly incorporated by reference in their entirety.

What is claimed is:

1. A method for depositing an aerosol onto a target surface comprising;

generating an aerosol, releasing an amount of aerosol into one end of an aerosol deposition chamber, actively propelling the aerosol toward the target surface located inside an aerosol deposition chamber, and striking the target surface with the aerosol, wherein the aerosol is selected from the group consisting of a bacteria, virus, spore, fungi, toxin, heavy metal, radioactive material, and aerosols mimicking them, wherein the aerosol is deposited on the target surface.

2. The method according to claim 1 wherein the aerosol is propelled laterally to a substantially vertical target surface.

3. A method for testing different techniques for removing an aerosol deposited contaminant from a surface comprising, subjecting an aerosol contaminated target surface to a first contaminant removing technique, subjecting another aerosol contaminated target surface to a second contaminant removing technique, determining the amount of aerosol contaminant remaining on each target surface after their respective contaminant removal techniques, and comparing the results, wherein the aerosol contaminated target surface was the target surface of claim 1.

4. An object having at least one target surface with aerosol deposited thereon by the method of claim 1 and removed from the aerosol deposition chamber.

5. An object of claim 4 wherein a gradient of deposited contaminant is present on the target surface.

6. A set of objects wherein at least two are substantially identical objects of claim 4.

7. A method for testing contaminant removal techniques, wherein the contaminant was delivered to a solid surface by aerosol, comprising;

applying a first contaminant removal technique to a first object in the set of claim 6, applying a different contaminant removal technique or a control technique to a second object of said set, and evaluating the effectiveness of said first contaminant removal technique.

8. A set of objects of claim 4 wherein at least two of the objects were produced by methods that differ from each other by one parameter selected from the group consisting of; composition of the aerosol, pressure of an aerosol containing gas, size of aerosolized particle, amount or concentration of substance in the aerosol particles, velocity of the aerosolized particles striking the target surface, distance before the aerosol strikes the target surface, dispersion pattern of aerosols on the target surface, atmospheric conditions and composition of the target surface.

9. A method for testing contaminant removal techniques, wherein the contaminant was delivered to a solid surface by aerosol, comprising;

applying a contaminant removal technique to at least two different objects in the set of claim 8, and evaluating the effectiveness of said contaminant removal technique.

10. A method for testing contaminant removal techniques, wherein the contaminant was delivered to a solid surface by aerosol, comprising;

applying a contaminant removal technique to the object of claim 4, and evaluating the effectiveness of said contaminant removal technique.

11. The method for testing contaminant removal techniques of claim 10 wherein the contaminant removal technique is selected from the group consisting of physically removing the contaminant, making the contaminant inert, and treating or coating the contaminant to prevent it from interacting with the surrounding environment.

* * * * *